United States Patent [19]

Man

[11] Patent Number: Plant 7,039

[45] Date of Patent: Sep. 19, 1989

[54] DISTINCT VARIETY OF BEGONIA PLANT NAMED APRIGOLD

[75] Inventor: Jan Man, Lisse, Netherlands

[73] Assignee: Oglevee Ltd., Connellsville, Pa.

[21] Appl. No.: 251,657

[22] Filed: Sep. 29, 1988

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Ziesenheim & Webb

[57] ABSTRACT

The new cultivar is generally characterized by its short compact form and extensive basal branching. Plant growth is vigorous. Flowers are brightly colored and clean in appearance. The plant is highly floriferous and the entire plant becomes covered with bloom. The new cultivar has a contrasting appearance from the dark foliage to the brightly colored orange hue with soft yellow-gold overtones of the bloom.

1 Drawing Sheet

BACKGROUND OF THE NEW PLANT

The present invention comprises a new and distinct cultivar of *Begonia*×*hiemalis* known by the varietal name of Aprigold. The new cultivar is a sport of the cultivar Marillo (U.S. patent application Ser. No. 07/251,658, filed Sept. 29, 1988). The new cultivar is similar in form and habit to Marillo. However, Aprigold is slightly shorter in height and while both cultivars have a base hue of orange, Aprigold has soft yellow-gold overtones whereas Marillo has pink overtones.

The new cultivar was discovered in August of 1985 at Limaplant b.v. in Lisse, Holland; was first asexually reproduced by cuttings at Limaplant by b.v. in Lisse, Holland; and has been repeatedly asexually reproduced by cuttings for Oglevee Ltd. in Connellsville, Pa. It has been found to retain its distinctive characteristics through successive propagations.

The new cultivar is generally characterized by its short compact form and extensive basal branching. Plant growth is vigorous. Flowers are brightly colored and clean in appearance. The plant is highly floriferous and the entire plant becomes covered with bloom. The new cultivar has a contrasting appearance from the dark foliage to the brightly colored orange hue with soft yellow-gold overtones of the bloom.

The new cultivar, when grown in a greenhouse in Connellsville, Pa., has a response time of 9 to 10 weeks from a well-rooted cutting to a flowering finished plant in a six inch pot (no pinch).

DESCRIPTION OF THE DRAWING

The accompanying drawing illustrates a new cultivar, the color being an nearly true as possible with color illustrations of this type.

DESCRIPTION OF THE NEW PLANT

The following detailed description sets forth the characteristics of the new cultivar. The data which define these characteristics were collected from asexual reproductions carried out for Oglevee Ltd. in Connellsville, Pa. The plant history was taken on ten week plants blossomed under natural light in a greenhouse and grown under temperature conditions of 68° F. night and day. The plants were potted Feb. 2, 1988 in a peat-lite mix and fertilized with a 150 ppm mixture of 20N-10P-20K. Color readings were taken indoors under 200 foot-candles of cool white fluorescent tubes. Color references are to the R.H.S. Colour Chart of The Royal Horticultural Society of London, unless noted differently.

Botanical classification: *Begonia*×*hiemalis.*

Flower:

*Fully expanded.*—5 cm. in diameter; side view: flattened oval appearance.

*Borne.*—Compound dichasium (cyme).

*Stems.*—Stems are strong and medium compact; main stem 0.5 to 1.5 cm in diameter; color yellow-green group 145B.

*Form.*—Semi-double to fully double. Each flower generally has 2 sepals, 5–6 petals, 3–6 petaloids (each group may vary ±1 structure).

*Permanence.*—Very long lasting bloom with average life of 2–3 weeks.

Color:

*Tonality from a distance.*—Base hue of orange with soft yellow-gold overtones.

*Front of petals.*—Color gradiant: Very outside margin of open bloom is yellow-orange group 17D. Color from outside edge to base of petal is orange group 25B.

*Reverse of petals.*—Characterized by Orange-Red group 32D and slightly lightening in intensity as base is approached.

*Base of petals.*—Very base is characterized by Green-yellow group 1D.

*Throat.*—None.

*Discoloration.*—None.

*Other comments.*—Bud color characterized by yellow-orange group 19C.

Petals:

*Texture.*—Crepe paper like (gentle crinkles).

*Appearance.*—Oval with color gradient. Outer edge: yellow-gold blending to soft orange.

*Arrangement.*—Semi-double to fully double.

*Persistence.*—Very good flowering response and long lasting.

*Fragrance.*—None observed.

Reproductive organs: All reproductive organs have modified into petaloids. Anthers, filament, pollen, style and ovaries could not be observed.

Plant:

*Form.*—Short compact, internodes (2–3 cm. apart); upright; good self-support strength, good basal branching.

*Growth.*—Very vigorous.

*Height from soil line.*—15–17 cm. in 10 weeks (no pinch, no cycocel).

*Spread.*—22–25 cm. in 10 weeks (no pinch, no cycocel).

Foliage:

*Size.*—Average length of 12 cm. and average width of 10 cm. from a leaf 3 nodes up from base of stem.

*Quantity.*—Very abundant.

*Shape.*—Acute tip with irregularly lobed attachment; edge is slightly doubly serrate.

*Top side.*—Green group 137A; shiny and smooth.

*Underside.*—Group group 138D.

*Ribs and veins.*—Smooth on top side, raised on lower side, lower side veins only area on leaf where visible tricomes (hairs) appear.

*Rib and vein color.*—Top side: Yellow-green group 146B; bottom: yellow-green group 146D.

*Margin.*—None.

*Stipules.*—None.

*Texture.*—Smooth, shiny and leathery.

I claim:

1. A new and distinct variety of begonia characterized by short compact form and extensive basal branching, vigorous plant growth and floriferousness and a contrasting orange hue with soft yellow-gold overtones bloom to the dark green foliage as herein shown and described.

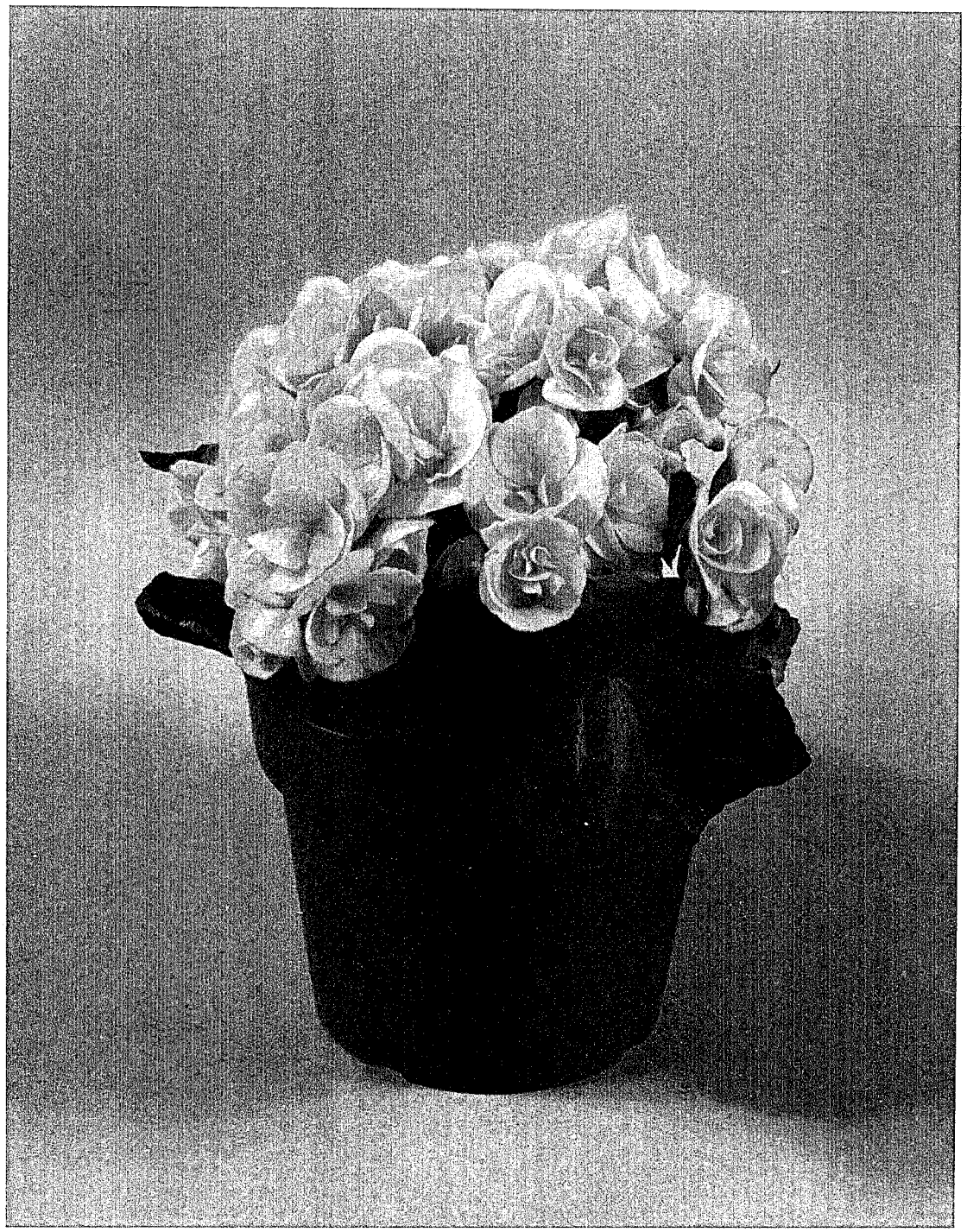

* * * * *